United States Patent [19]

Powers et al.

[11] Patent Number: 5,099,847
[45] Date of Patent: Mar. 31, 1992

[54] HIGH FRAME RATE ULTRASOUND SYSTEM

[75] Inventors: Jeffry E. Powers, Lake Stevens; Ronald E. Daigle, Redmond; Clifford R. Cooley, Seattle, all of Wash.

[73] Assignee: Advanced Technology Laboratories, Inc., Bothell, Wash.

[21] Appl. No.: 435,168

[22] Filed: Nov. 13, 1989

[51] Int. Cl.$^5$ .............................................. A61B 8/00
[52] U.S. Cl. .............................................. 128/660.07
[58] Field of Search .......................... 128/660.07; 73/625–626; 358/112

[56] References Cited

U.S. PATENT DOCUMENTS

| | | | |
|---|---|---|---|
| 3,954,098 | 5/1976 | Dick et al. | 128/660.07 X |
| 4,271,842 | 6/1981 | Specht et al. | 128/660.07 |
| 4,413,630 | 11/1983 | Anderson et al. | 128/660.07 X |
| 4,463,763 | 8/1984 | Koyano et al. | 128/660.07 X |
| 4,572,202 | 2/1986 | Thomenius | 128/660.07 |
| 4,846,188 | 7/1989 | Yoshioka | 128/661.01 |

Primary Examiner—Francis Jaworski

[57] ABSTRACT

A technique for increasing the display frame rate of a medical ultrasound imaging system. The system receives trigger signals, each based upon the occurrence of a predetermined event in a subject's cardiac cycle, such as an R-wave. In one technique, in response to each trigger signal, the ultrasound system acquires a series of frames, each frame comprising data representing an image of a portion of the subject's body at an associated acquisition time. A frame time is determined for each frame, each frame time being the time from the preceding trigger signal to the acquisition time for the frame. Two or more frame series are then played back in order of increasing frame times, thereby producing a display frame rate higher than the acquisition frame rate.

7 Claims, 4 Drawing Sheets

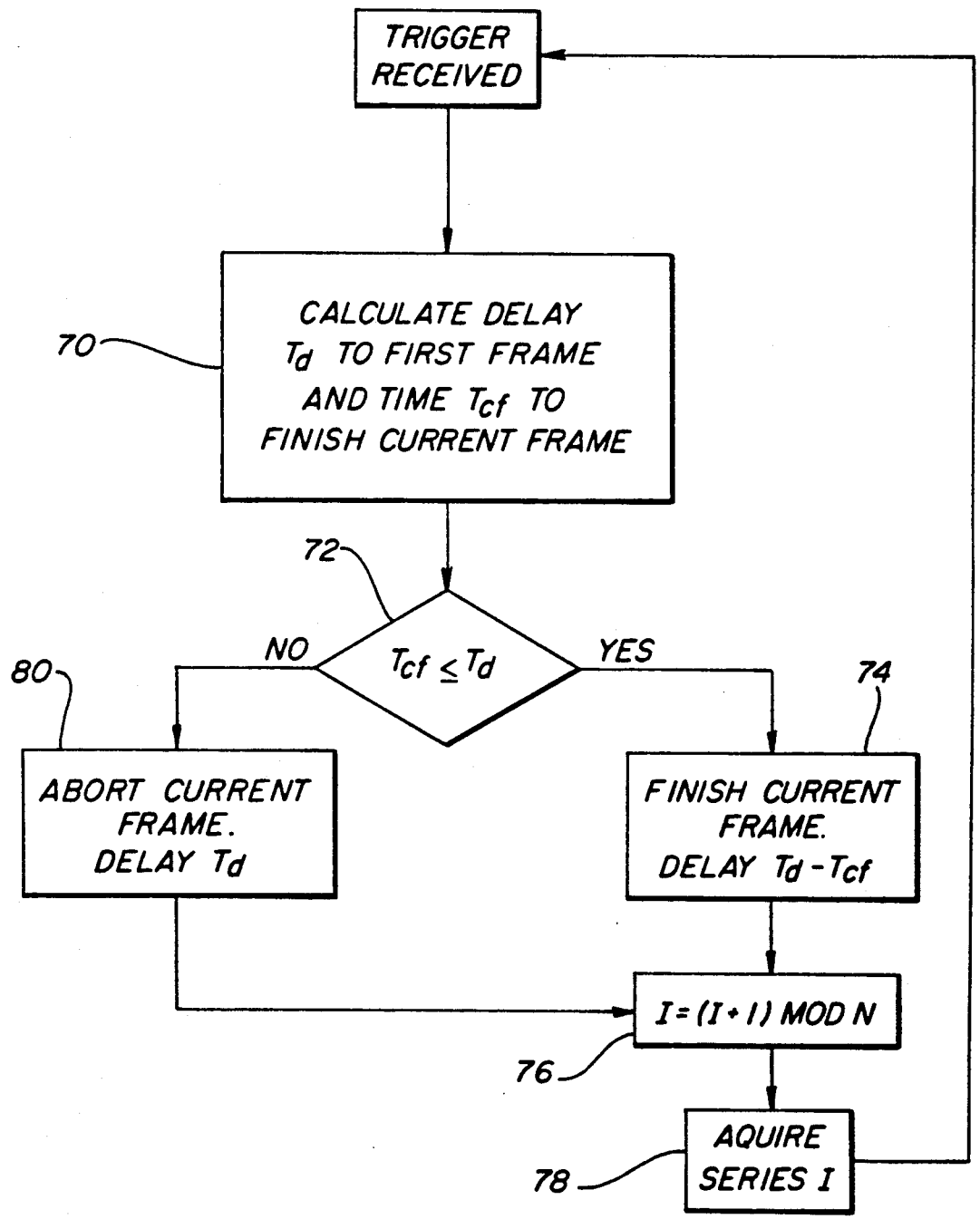

HIGH FRAME RATE ULTRASOUND SYSTEM

FIELD OF THE INVENTION

The present invention relates to medical ultrasound diagnostic devices and, in particular, to an ultrasound system that produces a video display of a region within a subject's body.

BACKGROUND OF THE INVENTION

Medical ultrasound scanners typically produce a two-dimensional grey scale image of a planar region of a subject's body. The grey scale image is created by transmitting a series of ultrasound pulses into the region under investigation, and receiving and processing the echoes of the transmitted pulses, to build up a two-dimensional image. Modern ultrasound scanners are capable of obtaining images at a fast enough rate, e.g., twenty or more times per second, so that a real time display of the region under investigation can be created on a video monitor.

Modern ultrasound systems generally include the capability of obtaining Doppler data from a selected volume within the two-dimensional region under investigation. The Doppler data represents the velocity of structures within the selected volume. Thus if the selected volume is within or includes a blood vessel, important information can be obtained concerning blood velocity. Such information is extremely useful in diagnosing various cardiac and other circulatory problems.

A relatively recent innovation in ultrasound systems is the use of "color flow" systems to combine a grey scale image and Doppler data. In a color flow system, all or a selected portion of a grey scale image is overlaid with a color image, with different colors corresponding to different velocities. Color flow systems must obtain Doppler data from a large number of sample volumes throughout a portion of an image. Since several pulses are required for each sample volume, the frame rate that can be obtained in color flow systems tends to be quite low. A low frame rate makes the display jerky, and can cause events of short time durations, such as small flow disturbances and valve leaks, to be missed entirely. There is therefore a substantial need for ultrasonic systems, particularly color flow systems, that are capable of producing frame rates high enough to provide real time imaging.

In a number of medical imaging systems, including CAT scans, MRI, PET, and thallium scanning with a gamma camera, it is known that imaging can sometimes be facilitated by taking advantage of the fact that the motion of a portion of the heart or circulatory system of a subject is substantially duplicated from one heartbeat to the next. Thus a number of such imaging techniques provide the ability to acquire a series of images or frames at fixed time delays after the occurrence of an R wave in an ECG signal. The acquisition is repeated for a number of subsequent cardiac cycles, and the results are then averaged and displayed. These techniques utilize a long integration time to produce a usable image or image set. However they have the effect of increasing acquisition time to produce a set of images at reasonable frame rates, rather than producing high frame rates in real time.

SUMMARY OF THE INVENTION

The present invention provides a technique for increasing the display frame rate of a medical ultrasound imaging system.

The ultrasound imaging system comprises signal acquisition means that includes means for transmitting ultrasound into a subject's body, and means for receiving echoes of the ultrasound energy and processing the echoes to produce a series of frames at an acquisition frame rate. Each frame comprises data representing an image of a portion of the subject's body at an associated acquisition time. The ultrasound imaging system further includes trigger means for generating a trigger signal based upon the occurrence of a predetermined event in the subject's cardiac cycle. For example, the trigger signal could be based upon the peak of the R wave of the subject's ECG signal. The system finally includes processing means that includes means for causing the signal acquisition means to produce a first series of frames subsequent to the generation of a first trigger signal and a second series of frames subsequent to the generation of a second trigger signal. The processing means also includes means for determining a frame time for each frame, each frame time corresponding to the time between the acquisition time for the frame and the preceding trigger signal. The frames are displayed in order of increasing frame times, enabling the ultrasound system to achieve a display frame rate that is higher than the acquisition frame rate.

In a preferred embodiment, each series of frames is acquired in response to, and at predetermined frame times with respect to, the preceding trigger signal. In this embodiment, the frame times are preferably staggered with one another, such that the frames are displayed in an interleaved fashion. The processing means preferably includes means for storing at least the first frames, display means for receiving frames and displaying the images represented thereby, and sequencing means for sending the first and second frames to the display means in order of increasing frame times.

BRIEF DESCRIPTION OF THE DRAWINGS

FIG. 5 is a flow chart illustrating the acquisition of frames when the ultrasound system is in triggered acquisition mode.

DETAILED DESCRIPTION OF THE PREFERRED EMBODIMENT

Figure 1:
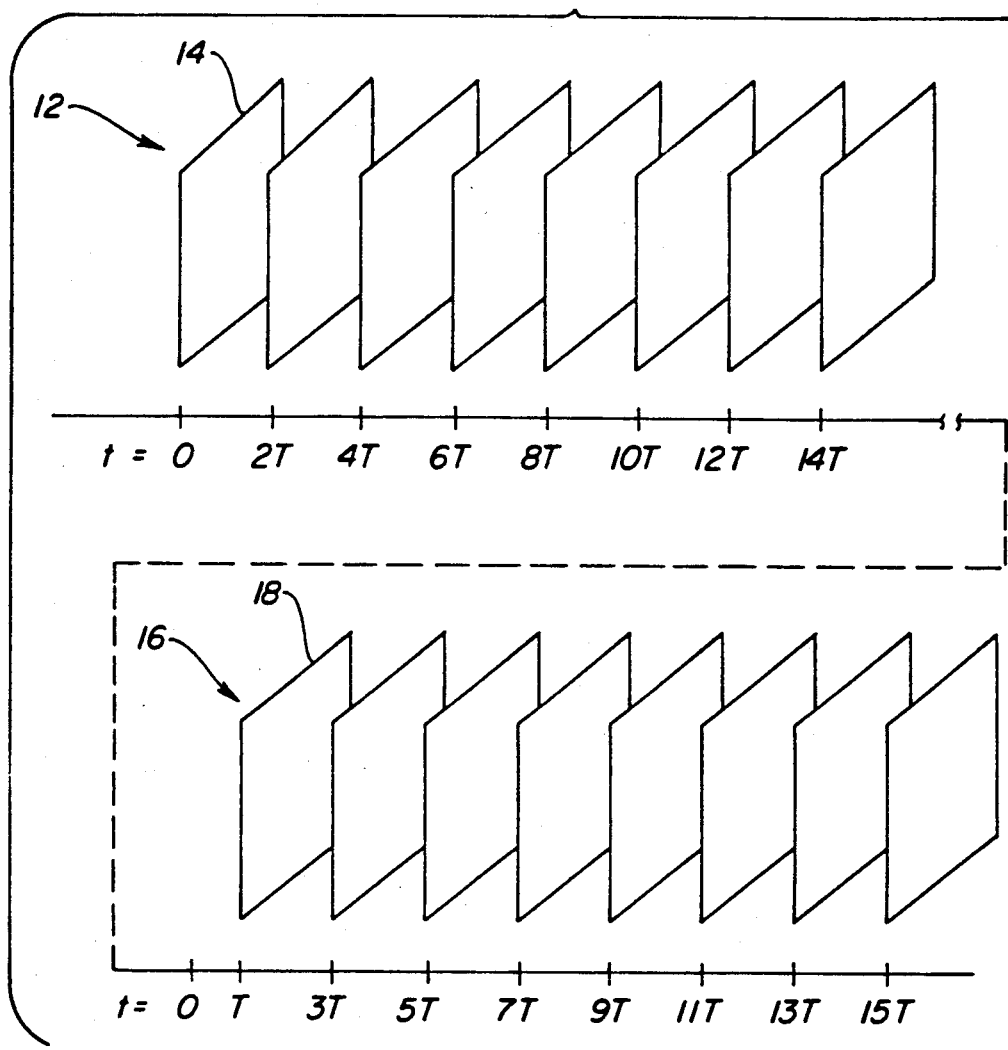
FIG. 1 illustrates the acquisition of video frames over two heart cycles, in accordance with the present invention.
Figure 2:
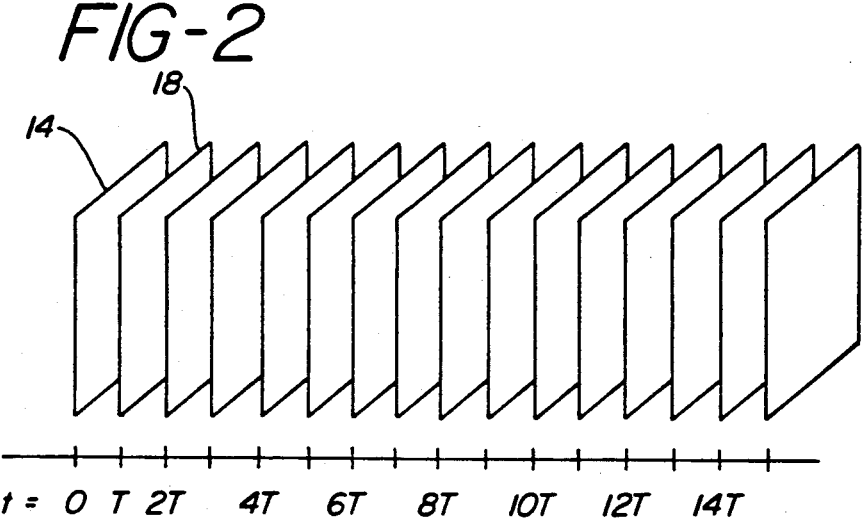
FIG. 2 illustrates the display sequence of the frames shown in FIG. 1.

The basic principle of a preferred embodiment of the present invention is illustrated in FIGS. 1 and 2. Referring initially to FIG. 1, the time t=0 is taken to be the time that each ECG trigger is received by the ultrasound system. Such a trigger can, for example, correspond to the peak of the R wave of the subject under examination. When a first trigger is received, the ultrasound system begins acquiring and storing a series 12 of frames 14 of video data, as shown in the upper half of FIG. 1. Each frame comprises data representing an image of a portion of the subject's body. In a color flow system, each frame includes both the grey scale image data and the associated Doppler data. Frames 14 are acquired at frame times t=0, 2T, 4T, etc., at an acquisition frame rate 1/(2T). The frame time for a frame can be defined as the time at which the generation of data for that frame commences. The acquisition of frames 14 continues until the next ECG trigger signal is received. At that time, as shown in the lower half of FIG. 1, the ultrasound system begins acquiring a second series 16 of frames 18. Frames 18 are acquired at frame times t=T, 3T, 5T, etc., at the same acquisition frame rate of 1/(2T), time t now being measured with respect to the second ECG trigger.

For the purpose of display, frames 14 and 18 shown in FIG. 1 are interleaved as shown in FIG. 2. Thus for display, the frames are sequenced in order of ascending frame times, with each frame time being measured with respect to its corresponding trigger signal. As a result, the display frame rate is 1/T, double the acquisition frame rate.

The system shown in FIGS. 1 and 2 can readily be extended to interleave frames from any number of consecutive cardiac cycles. Thus if N is the number of heart cycles that are to be interleaved to produce a single display sequence, then the first series of frames may be acquired at times 0, NT, 2NT, etc.; the second series of frames may be acquired at times T, (N+1)T, (2N+1)T, etc.; the third sequence of frames may be acquired at times 2T, (N+2)T, (2N+2)T, etc. As a result of such interleaving, the acquisition frame rate of 1/(NT) will be increased by a factor of N, to produce a display frame rate of 1/T.

The frame interleaving illustrated in FIGS. 1 and 2 can also be achieved in an untriggered mode. In an untriggered mode, the ultrasound system does not attempt to synchronize the acquisition of frames with the trigger signal. Instead, the system acquires N frame series at its normal acquisition frame rate. A frame time is determined for each frame, the frame time being the time from the preceding trigger signal to the frame's acquisition time. The frames of the N frame series are then played back in order of increasing frame times, as in the triggered mode described above. The advantage of the triggered mode is that the ultrasound system controls the frame times, so that equally spaced frame times can be produced, as shown in FIG. 2.

Figure 3:
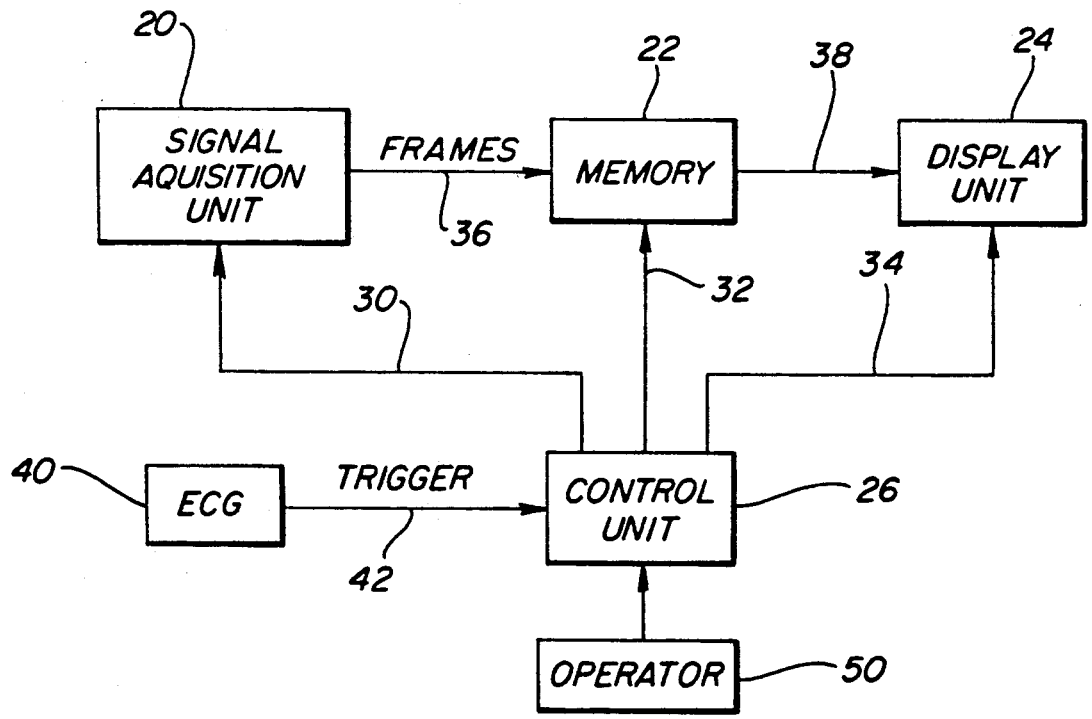
FIG. 3 is a block diagram of an ultrasound system for carrying out the present invention.

A preferred ultrasound system for implementing the present invention is illustrated in FIG. 3. The system includes signal acquisition unit 20, memory 22 and display unit 24. Operation of these units is controlled and coordinated by control unit 26 via lines 30, 32 and 34, respectively. An electrocardiograph (ECG) unit 40 is coupled to the control unit by line 42. ECG unit 40 may be provided as a separate instrument, or may form a part of the ultrasound system. The system as a whole is controlled by operator 50 via control unit 26.

Signal acquisition unit 20 includes an ultrasound transducer, or a transducer array, and a transmitter for driving the transducer so as to cause it to generate ultrasound that is radiated into a subject's body. The resulting echoes are then converted by the transducer into RF signals that are processed to provide focusing, beam steering, demodulation and other signal processing functions. The result of this processing is a processed signal on line 36 that contains information about the ultrasound reflections from an array of points within an image plane in the subject's body. In a color flow system, the processed signal includes information indicating the velocity of a plurality of points within the image plane. The processed signal is provided on line 36 as a series of frames, each frame comprising data representing one image of the subject's body at a particular acquisition time. Thus during color flow imaging, each frame includes the underlying grey scale image, as well as the velocity information to be superimposed thereon.

The frames on line 36 are written into memory 22, in a manner specified by a memory control signal on line 32. The storage of frames in memory 22 is described in greater detail below. When a given frame is to be displayed, the frame is read out of memory 22 onto line 38, for transmittal to display unit 24. Thus the interleaving of frames, as schematically shown in FIGS. 1 and 2, is accomplished by providing memory control signals in an appropriate sequence.

For operation in accordance with the present invention, the ultrasound system is connected to ECG unit 40 that is also connected to the subject under investigation. The ECG unit acquires an ECG signal representing the subject's electrocardiogram. ECG unit 40 processes the ECG signal, and produces a series of trigger signals on line 42 that are received by control unit 26 of the ultrasound system. Each trigger is produced in response to the occurrence of a predetermined feature of the ECG signal. Typically, such feature is the peak of the R wave, although any other identifiable feature could also be utilized.

Figure 4:
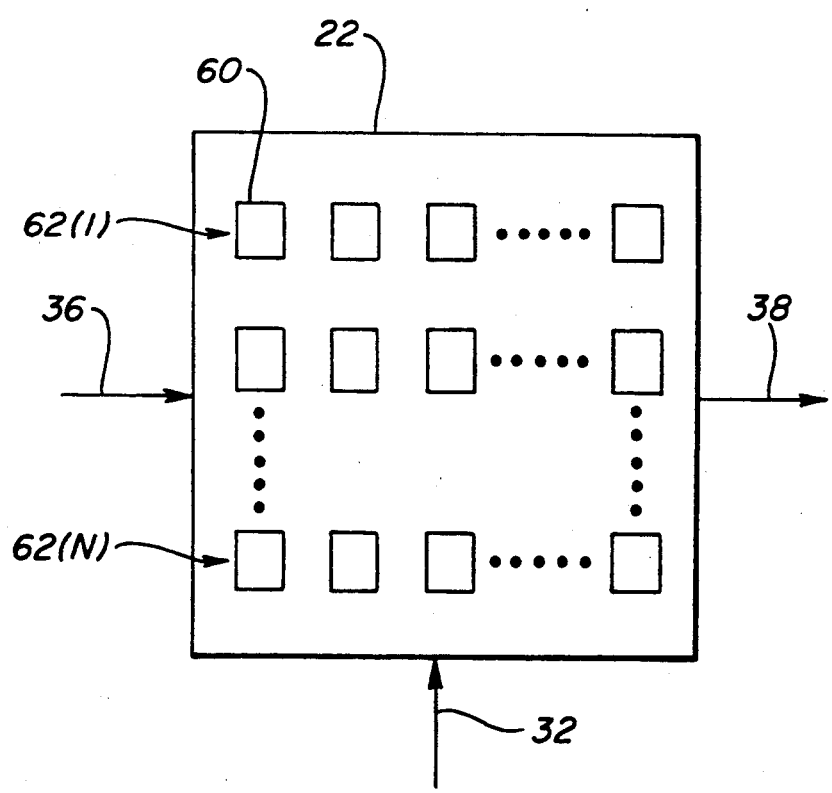
FIG. 4 is a schematic diagram of memory 22, showing the storage of frames therein.

In a preferred embodiment of the invention, the ultrasound system shown in FIG. 3 can be operated in two different modes. In a first mode, herein termed "real time" mode, operator 50 begins by entering a command that causes the system to activate the triggered acquisition operation of the present invention. The operator also enters at this time a number (N) designating the number of cardiac cycles to be interleaved, as described above. Alternately, the ultrasound system can compute N based upon the subject's heart rate, the frame rate, and the size of memory 22. The ultrasound system then proceeds to acquire N series of frames. Referring to FIG. 4, reference numeral 60 designates the data for a single frame, while reference numerals 62(1)–62(N) designates the N series of frames that are stored in memory 22. Thus each row in FIG. 4 represents frames for one frame series. Subsequently, as each frame series is produced on line 36, the frame series is stored in memory 22, overwriting the corresponding prior frame series. Once N series of frames are in memory 22, operator 50 can initiate the interleaved playback of the stored frames. The playback can be at a real time rate, in slow motion, one frame at a time, or in any other manner.

FIG. 5 illustrates the overall process of frame acquisition in triggered acquisition mode. Each time that control unit 26 receives a trigger signal on line 42 from the ECG unit, the control unit performs the steps indicated in block 70. In particular, the control unit calculates the delay $T_d$ to the first frame in the next series, as well as the time $T_{cf}$ required to finish the current frame. If the acquisition frame rate is designated FR, and if I designates the next frame series ($0 \leq I < N$), then the delay to the first frame in series I is equal to $I/(N \cdot FR)$. Thus for example referring to FIG. 1, the delay for series 12 is equal to 0, while the delay for series 16 is equal to T.

In block 72, the control means determines whether or not $T_{cf}$ is less than or equal to $T_d$. If so, then there is sufficient time to complete the current frame. As a result, the control means proceeds to block 74, finishes the current frame, and then waits for a delay equal to $T_d - T_{cf}$. The control means then proceeds in block 76 to update the value of I, and commences acquisition of sequence I in block 78. The acquisition of frame series I continues until the next ECG trigger is received.

If it is determined in block 72 that $T_{cf}$ is greater than $T_d$, there is not enough time to finish the current frame. As a result, the control means in block 80 aborts the current frame, waits for time $T_d$, and then proceeds to block 76 to begin acquisition of the new series. Acquisition of the new series continues until the next trigger is received, at which point the above-described process repeats.

In a second mode of operation, termed "freeze" mode, the ultrasound system operates in a manner generally similar to the first mode described above. However in freeze mode, after N series of frames have been stored in memory 22, the operator can enter a freeze command that suspends the writing of additional frames into memory 22. The "frozen" frames in memory 22 can then be played back in various manners, as described above. In freeze mode, control unit 26 can send a signal to the signal acquisition unit, causing the signal acquisition unit to suspend the production of new frames.

While the preferred embodiments of the invention have been illustrated and described, variations will be apparent to those skilled in the art. For example, the trigger signal could be derived from a pressure cuff attached to the subject, or could be based upon the maximum Doppler shift or the maximum brightness of an image feature, as measured by the ultrasound system. The latter technique may be especially useful for fetal imaging. In addition, while the process shown in FIG. 5 is preferred, the invention could be implemented by always aborting the current frame when a trigger signal is received. Accordingly, the scope of the invention is to be determined by reference to the following claims.

The embodiments of the invention in which an exclusive property or privilege is claimed are defined as follows:

1. A medical ultrasound imaging system, comprising:
   image frame acquisition means including means for transmitting ultrasound energy into a subject's body and means for receiving echoes of the ultrasound energy and processing the echoes to produce a series of frames at an acquisition frame rate, each frame comprising data representing an image of a portion of the subject's body at an associated acquisition time;
   trigger means for generating a trigger signal based upon the occurrence of a predetermined event in the subject's cardiac cycle;
   processing means including means for causing the signal acquisition means to produce
      a first series of frames acquired during a first cardiac cycle subsequent to the generation of a first trigger signal, wherein individual frames of said first series have respective acquisition time values related in time to the time of said first trigger signal, and
      a second series of frames acquired during a second cardiac cycle subsequent to the generation of a second trigger signal, wherein individual frames of said second series have respective acquisition time values related in time to the time of said second trigger signal and which differ from those of said first series; and
   means for displaying an interleaved sequence of frames of the first and second series of frames in the order of their acquisition time values relative to a trigger signal at a display frame rate which is equal to or greater than said acquisition frame rate.

2. The system of claim 1, wherein each series of frames is acquired in response to, and at predetermined acquisition times with respect to, the preceding trigger signal.

3. The system of claim 2, wherein N frame series are produced in response to N consecutive trigger signals, N being greater than 1, and wherein the acquisition times for the frames of the N frame series are evenly spaced in time from one another.

4. The system of claim 1, wherein the processing means comprises means for storing at least the first series of frames; and wherein said displaying means includes means for receiving frames and displaying the images represented thereby; and sequencing means for sending frames of the first and second series of frames to the receiving and displaying means in order of increasing acquisition times.

5. An imaging method for a medical ultrasound system that includes means for transmitting ultrasound energy into a subject's body and means for receiving echoes of the ultrasound energy and processing the echoes to produce a series of frames at an acquisition frame rate, each frame comprising data representing an image of a portion of the subject's body at an associated acquisition time, the method comprising:
   generating a recurring trigger signal based upon the occurrence of a predetermined event in the subject's cardiac cycle;
   causing the signal acquisition means to produce a first series of frames acquired during a first cardiac cycle subsequent to the generation of a first trigger signal, wherein respective frames have respective acquisition times relative to said first trigger signal;
   causing the signal acquisition means to produce a second series of frames acquired during a second cardiac cycle subsequent to the generation of a second trigger signal, wherein respective frames of said second series have respective acquisition times relative to said second trigger signal which differ from those of said first series; and
   displaying a sequence of frames of the first and second series of frames in order of increasing acquisition times relative to a trigger signal at a display frame rate which is equal to or greater than said acquisition frame rate.

6. The method of claim 5, wherein each series of frames is acquired in response to, and at predetermined acquisition times with respect to, the preceding trigger signal.

7. A medical ultrasound imaging system, comprising:
   image frame acquisition means including means for transmitting ultrasound energy into a subject's body and means for receiving echoes of the ultrasound energy and processing the echoes to produce a series of frames at an acquisition frame rate, each frame comprising data representing an image of a portion of the subject's body at an associated acquisition time;
   trigger means for generating a trigger signal based upon the occurrence of a predetermined event in the subject's cardiac cycle; and
   processing means including means for causing the signal acquisition means to produce a plurality of frames associated with first and second cardiac cycles subsequent to the occurrence of at least two trigger signals, and;

means for displaying the frames in order of increasing acquisition times at a display frame rate which is equal to or greater than said acquisition frame rate, wherein acquisition time is the time interval between the time of production of the frame and the preceding trigger signal.

* * * * *